United States Patent
Fan et al.

(10) Patent No.: US 9,862,731 B2
(45) Date of Patent: Jan. 9, 2018

(54) DIFLUOROBORON DIPYRROMETHENE FLUORESCENT PROBE, PRODUCTION METHOD AND APPLICATION THEREOF

(71) Applicant: DALIAN UNIVERSITY OF TECHNOLOGY, Dalian, Liaoning (CN)

(72) Inventors: Jiangli Fan, Liaoning (CN); Hao Zhu, Liaoning (CN); Xiaojun Peng, Liaoning (CN); Jingyun Wang, Liaoning (CN)

(73) Assignee: DALIAN UNIVERSITY OF TECHNOLOGY, Dalian, Liaoning (CN)

( * ) Notice: Subject to any disclaimer, the term of this patent is extended or adjusted under 35 U.S.C. 154(b) by 0 days.

(21) Appl. No.: 15/039,674

(22) PCT Filed: Nov. 26, 2014

(86) PCT No.: PCT/CN2014/092299
§ 371 (c)(1),
(2) Date: May 26, 2016

(87) PCT Pub. No.: WO2015/081803
PCT Pub. Date: Jun. 11, 2015

(65) Prior Publication Data
US 2017/0029444 A1    Feb. 2, 2017

(30) Foreign Application Priority Data
Dec. 2, 2013    (CN) .......................... 2013 1 0643027

(51) Int. Cl.
*C07F 5/02*    (2006.01)
*C09K 11/06*    (2006.01)
*G01N 33/58*    (2006.01)
*G01N 33/84*    (2006.01)

(52) U.S. Cl.
CPC ................ *C07F 5/022* (2013.01); *C07F 5/02* (2013.01); *C09K 11/06* (2013.01); *G01N 33/582* (2013.01); *G01N 33/84* (2013.01); *C09K 2211/1022* (2013.01); *C09K 2211/1029* (2013.01)

(58) Field of Classification Search
CPC ....................................................... C07F 5/02
See application file for complete search history.

(56) References Cited

FOREIGN PATENT DOCUMENTS

| CN | 1715919 A | 1/2006 |
|---|---|---|
| CN | 1944540 A | 4/2007 |
| CN | 101851500 A | 10/2010 |
| CN | 101883775 A | 11/2010 |
| CN | 102061103 A | 5/2011 |
| CN | 102702768 A | 10/2012 |
| CN | 102816826 A | 12/2012 |
| CN | 102993763 A | 3/2013 |
| JP | 2000001509 A | 1/2000 |
| JP | 2000039716 A | 2/2000 |
| JP | 2010520895 A | 6/2010 |
| KR | 20120110620 A | 10/2012 |

OTHER PUBLICATIONS

Cheng, Guanghui et al., "A highly specific BODIPY-based probe localized in mitochondria for HClO imaging", Analyst, vol. 138, No. 20, Jul. 25, 2013, pp. 6091-6096.
Zhu, Hao et al., An "Enhanced PET"-Based Fluorescent Probe with Ultrasensitivity for Imaging Basal and Elesclomol-Induced HClO in Cancer Cells, Journal of the American Chemical Society, vol. 136, No. 37, Aug. 29 2014, pp. 12820-12823.
Wu, Guangfei et al., "A water-soluble and specific BODIPY-based fluorescent", Analytical Methods, vol. 3, 2013, pp. 5589-5596.

*Primary Examiner* — Shawquia Jackson
(74) *Attorney, Agent, or Firm* — Novick, Kim & Lee, PLLC; Allen Xue

(57) ABSTRACT

The present invention provides a difluoroboron dipyrromethene fluorescent probe having a structure represented by the following general formula I, and a production method and an application thereof. Said difluoroboron dipyrromethene fluorescent probe exhibits low background fluorescence, and a rapid and significant fluorescence enhancement up to 100 times after the addition of hypochloric acid. The fluorescent intensity of said fluorescent probe shows a good linear relation with the concentration of hypochloric acid in a nanomole level, and the detection limit thereof is 0.56 nanomole. Said fluorescent probe has good selectivity since it hardly responds to other reactive oxygen species such as $H_2O_2$, $O_2^-$, TBHP, HO., TBO., $^1O_2$ and NO., and is not interfered by pH in a wide range. Said fluorescent probe can be applied to detect hypochloric acid in living cells.

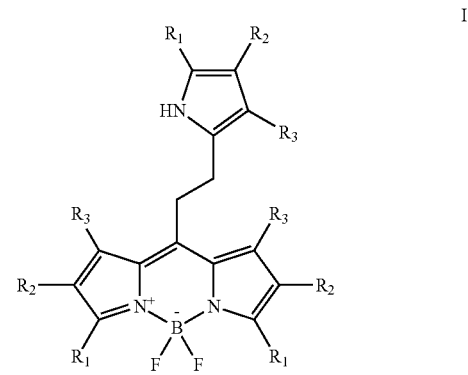

13 Claims, 5 Drawing Sheets

DIFLUOROBORON DIPYRROMETHENE FLUORESCENT PROBE, PRODUCTION METHOD AND APPLICATION THEREOF

FIELD OF THE INVENTION

The present invention relates to a fluorescent probe, and a production method and an application thereof, in the fine chemical field. Specifically, the present invention relates to a difluoroboron dipyrromethene fluorescent probe, and a production method and an application thereof in detecting hypochlorite ion.

DESCRIPTION OF THE RELATED ART

The fluorescent probe has been widely used as a functional dye in various fields of science and technology, and has been intensively studied particularly in life science, clinical diagnosis, immunological analysis and detection, and the like. Among many of the fluorescent dyes, the difluoroboron dipyrromethene (BDP) fluorescent dye possess many advantages such as relatively large molar extinction coefficient, high fluorescence quantum yield, stable spectroscopic property, good photothermal stability, good chemical stability, small molecular weight and relatively low cytotoxicity, and thus has been widely used as a biomolecule fluorescent probe, fluorescence imaging reagent or the like.

Hypochloric acid (HClO) is an important reactive oxygen species in organism, and physiologically, is mainly produced by a reaction between chloridion and hydrogen peroxide under the catalytic action of myeloperoxidase. In a cellular environment, hypochloric acid/hypochlorite ion can kill exotic bacteria due to their strong oxidability, thereby preventing invasion of the exotic bacteria and regulating cell life cycle. The level of hypochloric acid in human body gradually increases with age. However, the excessive hypochloric acid/hypochlorite ion may cause various diseases such as osteoarthritis, cardiovascular diseases and the like. Therefore, developing a method that can effectively monitor hypochloric acid attracts the attention of the researchers more and more.

In recent years, the researchers have developed various fluorescent probes that can be applied to detect hypochloric acid/hypochlorite ion in an aqueous solution or organism. These probes have been developed mainly based on the strong oxidability of hypochloric acid, for example, based on dibenzoylhydrazine oxidation mechanism, hydroximic acid oxidation mechanism, deoximation mechanism, p-methoxyphenol oxidation mechanism, sulfur atom oxidation mechanism, and the like. However, these probes generally have shortcomings such as long response time, low sensitivity, poor selectivity, susceptibility to pH interference and the like. Pyrrole is an important material for synthesizing BDP. The inventors have found that pyrrole can be selectively oxidized by hypochloric acid but is insensitive to other reactive oxygen species (e.g. $H_2O_2$, .OH or the like). Moreover, pyrrole has aromaticity and the unshared electron pair on nitrogen atom thereof participates to constitute the cyclic $\pi$ bond, which weakens its ability to combine with proton and thus protects it from the pH interference. Besides these, the electron-rich property of pyrrole can effectively induce the photoinduced electron transfer (PET) effect to some fluorophores, thereby decreasing the background fluorescence and improving the probe sensitivity.

SUMMARY OF THE INVENTION

In order to overcome the above-mentioned shortcomings such as long response time, low sensitivity, poor selectivity, susceptibility to pH interference and the like of the fluorescent probe in the detection of hypochlorite ion in the prior art, an object of the present invention is to provide a difluoroboron dipyrromethene fluorescent probe which has 2,4-dimethylpyrrole as a recognition group and a difluoroboron dipyrromethene moiety as a fluorophore, with improved probe selectivity (not interfered by other reactive oxygen species and pH) and sensitivity, shortened response time and promising bioapplication prospect.

The technical object of the present invention will be achieved based on the following technical means.

The present invention provides a difluoroboron dipyrromethene fluorescent probe having the following general formula I:

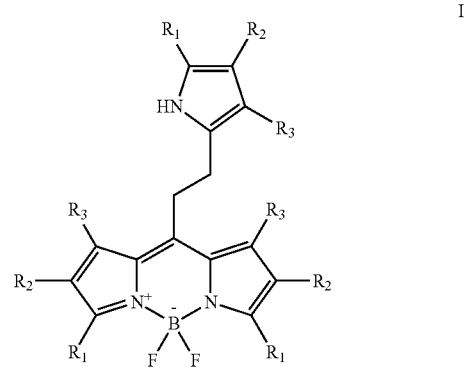

wherein in the general formula I, $R_1$, $R_2$ and $R_3$ are each independently selected from the group consisting of H, $C_{1-8}$ alkyl, and substituted or unsubstituted phenyl, and said substituted phenyl is substituted at an optional location with one or more substituents selected from the group consisting of CN, COOH, $NH_2$, $NO_2$, OH, SH, $C_{1-6}$ alkoxy, $C_{1-6}$ alkylamino, $C_{1-6}$ amido, halogen and $C_{1-6}$ haloalkyl.

The present invention also provides a method for producing said difluoroboron dipyrromethene fluorescent probe, comprising the steps of:

reacting a compound having the following general formula II with acryloyl chloride in a molar ratio ranging from 1:1 to 5:1, and

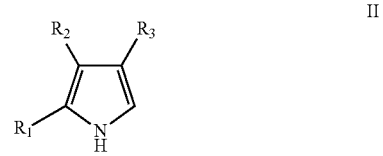

complexing the resultant reaction product with boron trifluoride in the presence of a base to obtain said difluoroboron dipyrromethene fluorescent probe.

The present invention further provides an application of said difluoroboron dipyrromethene fluorescent probe in detecting hypochlorite ion.

Said difluoroboron dipyrromethene fluorescent probe of the present invention has the following advantageous technical effects:

(1) Said fluorescent probe hardly emits fluorescence in an aqueous solution, which decreases the background fluorescence in the detection;

(2) Said fluorescent probe exhibits high sensitivity, since its fluorescence increases remarkably in the presence of hypochloric acid/hypochlorite ion in a nanomole level, and its fluorescent intensity enhancement shows a good linear relation with the level of hypochloric acid;

(3) Said fluorescent probe exhibits good selectivity, since it hardly responds to other reactive oxygen species such as $H_2O_2$, —OH and the like;

(4) Said fluorescent probe responds rapidly, since its fluorescent intensity reaches equilibrium in seconds after the addition of hypochloric acid;

(5) Said fluorescent probe shows accurate result in the detection of hypochloric acid in a pH range of 4.0 to 9.0, and thus is not interfered by pH; and (6) Said fluorescent probe is easily synthesized, and thus the product is easily obtained.

BRIEF DESCRIPTION OF THE DRAWINGS

Seven figures are shown in the present specification.

FIG. 1, panel a is a fluorescence titration spectrum of BClO versus sodium hypochlorite at an excitation wavelength of 480 nm, and FIG. 1, panel b is a titration curve of BClO versus sodium hypochlorite at an excitation wavelength of 480 nm.

FIG. 7, panels a, b and c are fluorescence pictures of BClO collected at a wavelength range from 490 nm to 550 nm in cells in which 0, 3 or 5 μM of sodium hypochlorite has been added, respectively. The excitation wavelength is 488 nm. The statistic analysis based on double sample test was carried out, and the fluorescent intensity at 0 μM of sodium hypochlorite level was used as a standard. ***P<0.001, and the error bar indicates mean standard error (n=10).

FIG. 8, panel a is a cell fluorescence picture after the addition of BClO, and FIG. 8, panel b is a cell fluorescence picture obtained by incubating Raw264.7 cells with 1 μg/mL of LPS (lipopolysaccharide) for 12 hours and then incubating Raw264.7 cells with 1 μg/mL of PMA (phorbol myristate acetate) for 1 hour, followed by adding BClO. The fluorescence at a wavelength range from 490 nm to 550 nm was collected. The excitation wavelength is 488 nm. The statistic analysis based on double sample test was carried out, and the fluorescent intensity when only BClO was added was used as a standard. ***P<0.001, and the error bar indicates mean standard error (n=4).

DESCRIPTION OF THE PREFERRED EMBODIMENT

Figure 1:
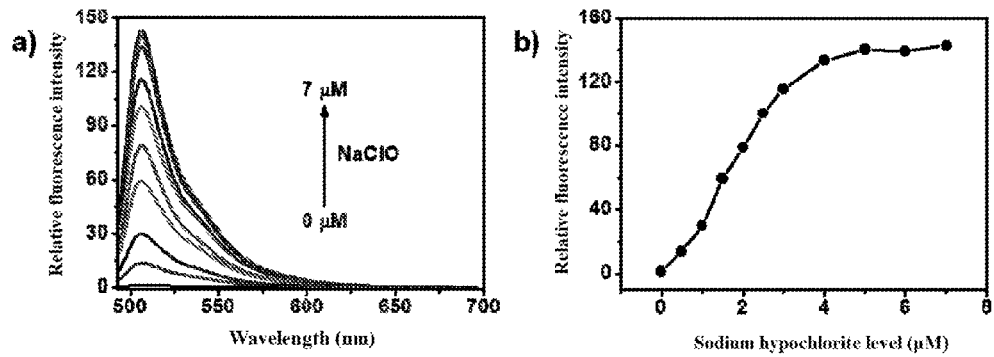
FIG. 1 is a figure showing fluorescent intensities of the fluorescent probe BClO versus various levels of hypochlorite ion in the BClO performance measurement experiment 1. The level of the probe BClO is 1 μM, the levels of sodium hypochlorite are 0, 1, 2, 3, 4, 5, 6 and 7 μM, respectively, and the measurement system is a phosphate buffer solution (containing ethanol in a volume ratio of 10% as a dye cosolvent, pH=7.4).

The present invention provides a difluoroboron dipyrromethene fluorescent probe having the following general formula I:

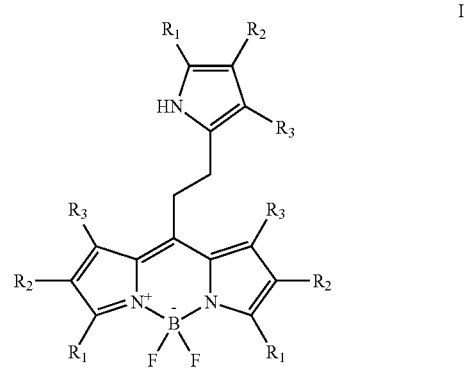

wherein in the general formula I, $R_1$, $R_2$ and $R_3$ are each independently selected from the group consisting of H, $C_{1-8}$ alkyl, and substituted or unsubstituted phenyl, and said substituted phenyl is substituted at an optional location with one or more substituents selected from the group consisting of CN, COOH, $NH_2$, $NO_2$, OH, SH, $C_{1-6}$ alkoxy, $C_{1-6}$ alkylamino, $C_{1-6}$ amido, halogen and $C_{1-6}$ haloalkyl.

In a preferable embodiment, in the general formula I of said difluoroboron dipyrromethene fluorescent probe according to the present invention, said $R_1$ and $R_3$ are each independently selected from the group consisting of H and methyl, and are more preferably methyl; and said $R_2$ is preferably selected from the group consisting of H and ethyl, and is more preferably H.

In a most preferable embodiment, said difluoroboron dipyrromethene fluorescent probe of the present invention is BClO, which has the following structure.

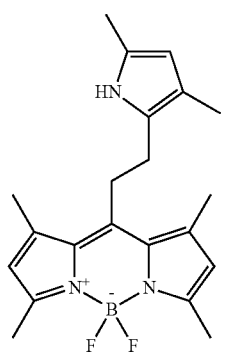

The present invention further provides a method for producing said difluoroboron dipyrromethene fluorescent probe, comprising the steps of:

reacting a compound having the following general formula II with acryloyl chloride in a molar ratio ranging from 1:1 to 5:1, and

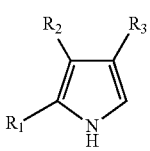

complexing the resultant reaction product with boron trifluoride in the presence of a base to obtain said difluoroboron dipyrromethene fluorescent probe.

Specific embodiments of said production method according to the present invention are as follows.

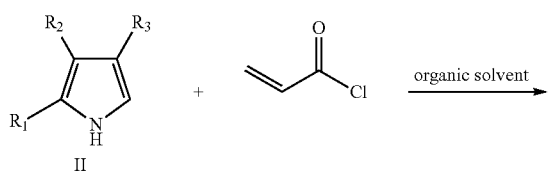

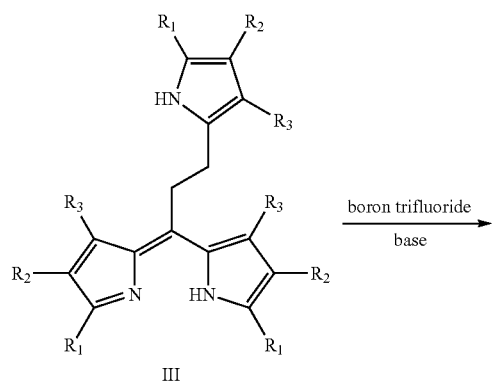

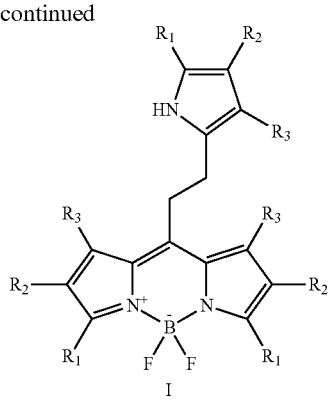

(1) An intermediate compound III is prepared by reacting a compound having the general formula II with acryloyl chloride, wherein a molar ratio of the compound II to acryloyl chloride may range from 0.1:1 to 1000:1, preferably ranges from 0.5:1 to 100:1, more preferably ranges from 0.5:1 to 10:1, even more preferably ranges from 1:1 to 5:1, and is most preferably 3:1. In this reaction, the compound II and acryloyl chloride are condensed to obtain the compound having the general formula III.

The reaction may be carried out in an organic solvent containing water or an organic solvent not containing water. The organic solvent not containing water is preferred. The molar concentration of the pyrrole material in the solvent ranges from 0.012 to 0.4 mol/L. Examples of the organic solvent include, but not limited to, dichloromethane, tetrahydrofuran, acetonitrile, and the like. In the reaction, the pyrrole material and acryloyl chloride are condensed for two times to obtain the active intermediate III. The product is unstable and thus it can be directly used for the next reaction without purification. Completion of the reaction may be monitored by thin layer chromatography (TLC) during the reaction.

The reaction temperature should be controlled in a range from 15° C. to 120° C. This is because pyrrole molecules tend to be self-polymerized to form a sticky brown material at a high temperature, which influences the main reaction and greatly reduces the yield. On the other hand, if the reaction temperature is excessively low, a long time would be taken to ensure sufficient reaction. Therefore, the reaction temperature preferably ranges from 30° C. to 100° C., more preferably ranges from 30° C. to 80° C., most preferably ranges from 40° C. to 60° C.

(2) Said difluoroboron dipyrromethene fluorescent probe is synthesized. Dehydrofluorination reaction occurs between the intermediate III obtained in the step (1) and a boron trifluoride compound in the presence of an organic base to form the product that is the compound having the formula I. The boron trifluoride compound to be added may be a boron trifluoride gas, boron trifluoride ethyl ether complex or any compound capable of releasing boron trifluoride in a solution at normal temperature.

The reaction temperature ranges from −10° C. to 100° C., preferably ranges from 0° C. to 10° C. When the boron trifluoride compound (e.g. boron trifluoride gas or boron trifluoride complex) is added, an organic base is needed to promote the reaction. Said organic base is preferably triethylamine.

The method for purifying said difluoroboron dipyrromethene fluorescent dye of the present invention is not particularly limited, and a conventional method may be utilized. Generally, when the reaction is completed, the solvent will be distilled off. Column chromatography using petroleum ether/ethyl acetate as an eluent is preferably utilized to purify the product.

The obtained fluorescent dye may be recovered by a conventional separation/purification method in the art to reach a desired purity.

All the materials used in the present invention are commercially available, or can be easily prepared from conventional materials in the art with conventional methods known by a person having ordinary skill in the art or methods disclosed in the prior art.

It should be noted that some of the substituents on the ring of the compounds in the present invention may be introduced by a standard aromatic substitution reaction or be generated by a conventional functional group modification before the above-mentioned steps or immediately after the above-mentioned steps, and such reaction and modification are included in the method of the present invention. Examples of the reaction and modification include substituent introduction based on an aromatic substitution reaction, substituent reduction, substituent alkylation, and substituent oxidation. The reagent and reaction conditions for these processes are conventional in the chemical field. Specific examples of the aromatic substitution reaction include nitro introduction by using concentrated nitric acid, acyl introduction by using acyl halide, Lewis acid (e.g. aluminum trichloride) or the like under the condition of Friedel Crafts, alkyl introduction by using alkyl halide, Lewis acid (e.g. aluminum trichloride) or the like under the condition of Friedel Crafts, and halogen introduction. Specific examples of the modification include a method of reducing nitro to amino by hydrogenation using nickel catalyst or the like, or by a heat-treatment in the presence of hydrochloric acid and iron; and a method of oxidizing alkylthio to alkylsulfinyl or alkylsulfonyl.

The terms described in the present specification have the following definitions, unless otherwise stated.

The term "alkyl" described in the present specification includes a linear alkyl and a branched alkyl. The specifically mentioned single alkyl such as "propyl" specifically means a linear alkyl, and the specifically mentioned single branched alkyl such as "isopropyl" specifically means a branched alkyl. For example, "$C_{1-4}$ alkyl" includes methyl, ethyl, n-propyl, isopropyl, n-butyl, t-butyl and the like. The same rationale also applies to other group described in the present specification.

Said difluoroboron dipyrromethene fluorescent probe of the present invention can be applied to detect hypochlorite ion, especially to detect hypochlorite ion in living cells.

The following non-limiting examples are used to help a person having ordinary skill in the art to fully understand the present invention, but not to in any way limit the present invention.

EXAMPLES

Example 1

Synthesis of Fluorescent Probe BClO

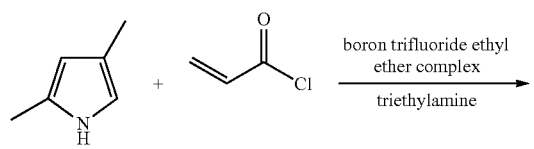

-continued

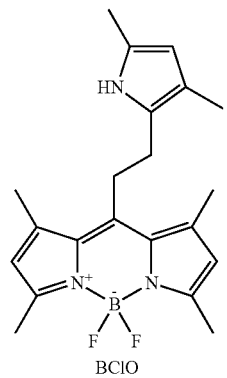

BClO

Into a 500 mL single-neck flask containing 250 mL of dichloromethane, 2,4-dimethylpyrrole (2.8 g, 30 mmol) was added, and then acryloyl chloride (0.9 g, 10 mmol) was added, the resultant mixture was stirred overnight at 50° C. in a dark place under the protection of nitrogen. Under the condition of an icewater bath, 10 mL of triethylamine and 10 mL of boron trifluoride ethyl ether complex were added dropwise to the mixture, and continued to be stirred for 1 hour. The solvent was distilled off under a reduced pressure, and purification was carried out using column chromatography to obtain an orange solid BClO (9.6%). $^1$H NMR (400 MHz, CDCl$_3$), δ:1.96 (s, 3H), 2.17 (s, 3H), 2.35 (s, 6H), 2.53 (s, 6H), 2.84 (t, J=8 Hz, 2H), 3.17 (t, J=8 Hz, 2H), 5.62 (s, 1H), 6.04 (s, 2H), 7.43 (s, 1H); $^{13}$C NMR (100 MHz, CDCl$_3$), δ:11.1, 13.0, 14.6, 16.2, 27.4, 29.9, 107.8, 114.5, 121.9, 124.0, 126.3, 131.5, 141.2, 145.5, 154.1 ppm; TOF MS: m/z calcd for $C_{21}H_{27}BF_2N_3^+$[M+H]$^+$: 370.2216. found: 370.2255.

BClO Performance Measurement Experiment 1

Fluorescence Titration Experiment of Fluorescent Probe BClO in Detecting Hypochlorite Ion Into a phosphate buffer solution (containing ethanol in a volume ratio of 10% as a dye cosolvent, pH=7.4), 1 μM of the probe BClO was added, and then a sodium hypochlorite solution was added therein dropwise in a final level of 0, 1, 2, 3, 4, 5, 6 or 7 μM of hypochlorite ion, respectively, the fluorescent intensities at an excitation wavelength of 480 nm were recorded. The measurement results are shown in FIG. 1, panel a and panel b. It can be seen from the figures that the fluorescent intensity of the probe at the maximum emission peak of 505 nm gradually increases with the increase of the sodium hypochlorite level, and reaches saturation when the sodium hypochlorite level is 5 μM.

BClO Performance Measurement Experiment 2

Figure 2:
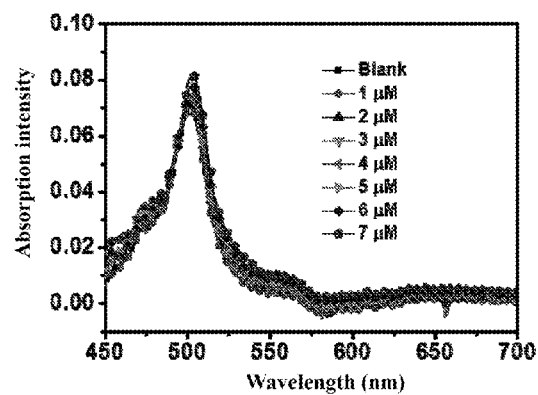
FIG. 2 is a figure showing absorption titration results of the fluorescent probe BClO versus various levels of hypochlorite ion in the BClO performance measurement experiment 2. The level of the fluorescent probe BClO is 1 μM, and the levels of sodium hypochlorite are 0, 1, 2, 3, 4, 5, 6 and 7 μM, respectively.

Absorption Titration Experiment of Fluorescent Probe BClO in Detecting Hypochlorite Ion Into a phosphate buffer solution (containing ethanol in a volume ratio of 10% as a dye cosolvent, pH=7.4), 1 μM of the probe BClO was added, and then a sodium hypochlorite solution was added therein dropwise in a final level of 0, 1, 2, 3, 4, 5, 6 or 7 μM of hypochlorite ion, respectively, the fluorescent intensities were recorded. The measurement results are shown in FIG. 2. It can be seen from the figure that the absorption spectra of the probe are nearly kept same with the increase of the sodium hypochlorite level.

BClO Performance Measurement Experiment 3

Selectivity Experiment of Fluorescent Probe BClO in Detecting Hypochlorite Ion

Figure 3:
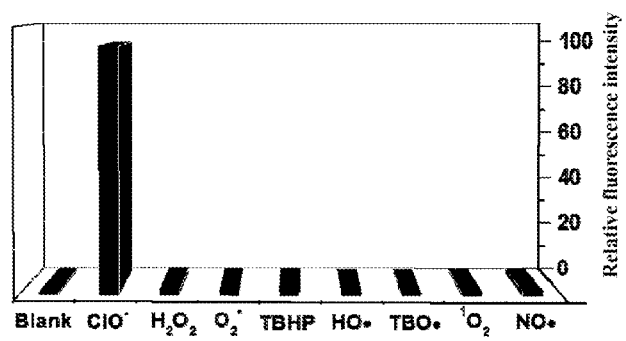
FIG. 3 is a histogram showing fluorescence selectivity of the fluorescent probe BClO to various reactive oxygen species in the BClO performance measurement experiment 3. The level of the fluorescent probe BClO is 1 μM, the level of sodium hypochlorite is 5 μM, and the level of other reactive oxygen species is 10 μM, respectively.

The above-synthesized compound BClO was used to evaluate the selectivity of the fluorescent probe to hypochlorite ion and reactive oxygen species. Specifically, 1 µM of the compound BClO was added into a phosphate buffer solution (containing ethanol in a volume ratio of 10% as a dye cosolvent, pH=7.4) in which 5 µM of hypochlorite ion or 10 µM of other reactive oxygen species ($H_2O_2$, $O_2^-$, TBHP, HO., TBO., $^1O_2$, NO.) was included, and the corresponding fluorescent intensities at an excitation wavelength of 480 nm and an emission wavelength of 505 nm were recorded. The measurement results are shown in FIG. 3. It can be seen from the figure that the fluorescent probe BClO has very good selectivity to sodium hypochlorite, because the addition of 5 µM of sodium hypochlorite significantly enhances the fluorescent intensity of BClO (100 times), while the addition of other reactive oxygen species does not significantly enhance the fluorescent intensity of BClO.

Figure 4:
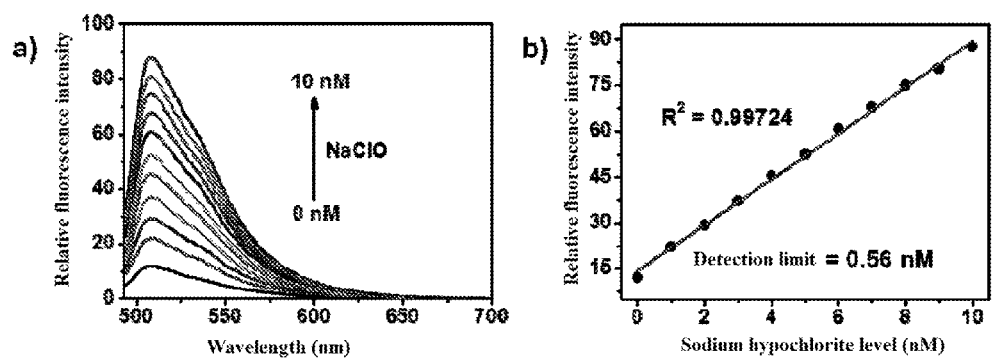
FIG. 4 is a figure showing fluorescent intensity response of the fluorescent probe BClO versus hypochlorite ion in a low level in the BClO performance measurement experiment 4. The level of the fluorescent probe BClO is 1 μM, and the levels of sodium hypochlorite are 0, 1, 2, 3, 4, 5, 6, 7, 8, 9 and 10 nM, respectively.

BClO Performance Measurement Experiment 4
Sensitivity of Fluorescent Probe BClO in Detecting Hypochlorite Ion The above-synthesized compound BClO was used to evaluate the response of the fluorescent probe to hypochlorite ion in a nanomole level. Specifically, the compound BClO (1 µM) was added into a phosphate buffer solution (containing ethanol in a volume ratio of 10% as a dye cosolvent, pH=7.4) in which sodium hypochlorite in a level of 0, 1, 2, 3, 4, 5, 6, 7, 8, 9 or 10 nM was included, and the corresponding fluorescence spectra excited at 480 nm and the fluorescent intensities emitted at 505 nm were recorded. The measurement results are shown in FIG. 4. It can be seen from the figures that the fluorescent intensity of the fluorescent probe BClO significantly enhances when the level of hypochlorite ion is in a range from 0 to 10 nM, and has a good linear relation with the change of sodium hypochlorite level ($R^2=0.99724$). Thus, the fluorescent probe BClO can be applied to detect sodium hypochlorite in a low level, and the detection limit thereof is 0.56 nM according to $3\sigma/k$ calculation.

Figure 5:
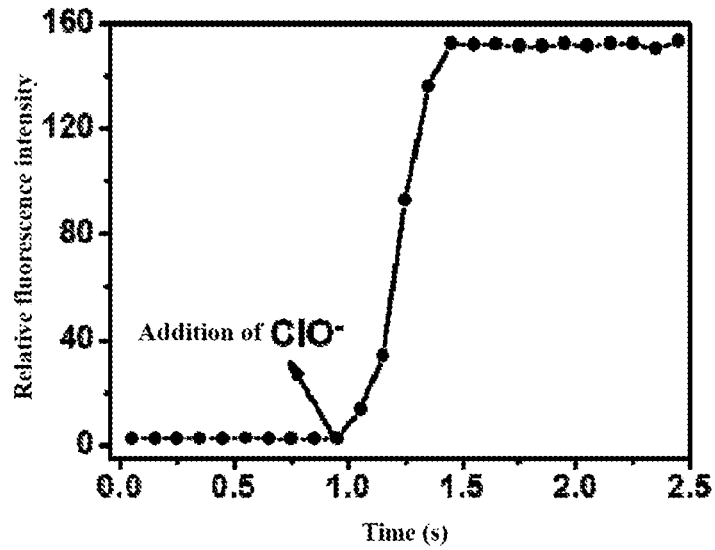
FIG. 5 is a figure showing response time of the fluorescent probe BClO in the detection of sodium hypochlorite in the BClO performance measurement experiment 5. The level of the fluorescent probe BClO is 1 μM, and the level of sodium hypochlorite is 5 μM. The horizontal axis is time(s), and the vertical axis is fluorescent intensity.

BClO Performance Measurement Experiment 5
Response Time Measurement of Probe BClO in Detecting Hypochlorite Ion FIG. 5 shows a time function of the probe BClO in the detection of hypochlorite ion. The level of the probe BClO was 1 µM, the measurement system was a phosphate buffer solution (containing ethanol in a volume ratio of 10% as a dye cosolvent, pH=7.4), and the excitation wavelength was 480 nm. The fluorescent intensities of BClO at 505 nm versus time were recorded. It can be seen from FIG. 5 that BClO responds very rapidly to hypochlorite ion, and the fluorescent intensity thereof reaches equilibrium in one second. The horizontal axis is time (second), and the vertical axis is fluorescent intensity.

Figure 6:
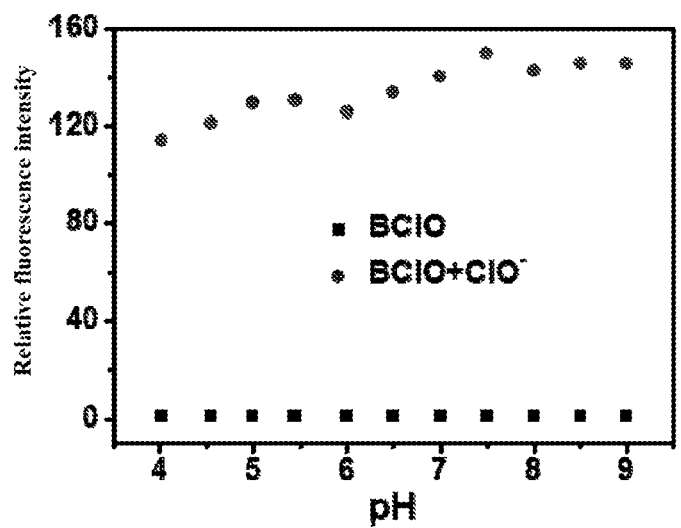
FIG. 6 is a figure showing fluorescent intensity response of the probe BClO versus hypochlorite ion in various pH conditions in the BClO performance measurement experiment 6. The horizontal axis is pH, and the vertical axis is fluorescent intensity. The level of the fluorescent probe BClO is 1 μM, and the level of sodium hypochlorite is 5 μM. NaOH (1M) or HCl (1M) was used to adjust pH.

BClO Performance Measurement Experiment 6
Study on pH Interference to Probe BClO in Detecting Hypochlorite Ion The above-synthesized compound BClO was used to evaluate the response of the fluorescent probe to pH. A phosphate buffer solution (containing ethanol in a volume ratio of 10% as a dye cosolvent) in which the compound BClO (1 µM) was included, was adjusted to about pH 4.0, and the fluorescent intensities of the probe before and after the addition of 5 µM of sodium hypochlorite were measured at an excitation wavelength of 480 nm. Then, an alkaline solution was added therein to gradually increase pH to about 9.0, and the corresponding fluorescent intensity changes were recorded. The measurement results are shown in FIG. 6. It can be seen from the figure that pH change in a range from 4.0 to 9.0 hardly has an influence on the fluorescence emission of the fluorescent probe BClO before and after the addition of sodium hypochlorite. Thus, the probe BClO can be applied to detect hypochlorite ion in the above pH range. The horizontal axis is pH, and the vertical axis is fluorescent intensity. In the experiment, NaOH (1M) or HCl (1M) was used to adjust pH.

BClO Performance Measurement Experiment 7
Study on Probe BClO in Detecting Hypochlorite Ion in Various Levels in MCF-7 Cells MCF-7 cells were cultured in DEME (invitrogen) containing 10% FCS (invitrogen). On the day before the fluorescence confocal imaging experiment, the cells were inoculated in a specialized confocal cell culture dish. On the next day, 1 µM of the probe BClO was added therein, the cells were incubated for 20 minutes under the conditions of 37° C. and 5% $CO_2$ and then rinsed with a phosphate buffer solution for three times, and the confocal imaging was carried out. Under the same conditions, 3 µM or 5 µM of sodium hypochlorite was further added, and the confocal imaging was carried out immediately.

The culture density of cells was $2\times10^5$ cells/mL. The imaging instrument was Olympus FV1000-IX81 inverted microscope with oil lens of 100 times magnification. The fluorescence was exited at 488 nm, and the fluorescence at a wavelength range from 490 to 550 nm was collected.

Figure 7:
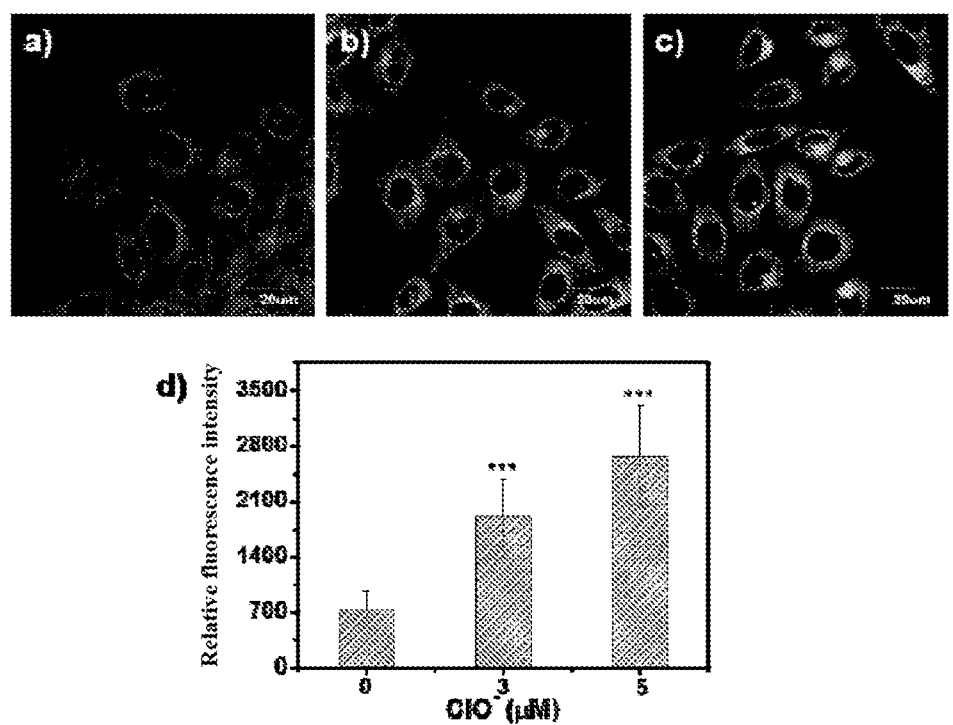
FIG. 7 shows fluorescence imaging pictures of the probe BClO in human breast cancer (MCF-7) cells in the BClO performance measurement experiment 7. The level of the fluorescent probe BClO is 1 μM.

FIG. 7, panels a, b, and c are fluorescence pictures of BClO in living cells before and after the addition of sodium hypochlorite. In order to quantify the fluorescent intensity change of BClO in cells, ten regions were chosen from each figure to calculate the average value of the relative fluorescent intensity, and the results are shown in FIG. 7, panel d. It can be seen from the figure that, the probe BClO emits weak green fluorescence in cells before the addition of sodium hypochlorite due to a certain amount of reactive oxygen species present in MCF-7 cells, while the fluorescent intensity of the probe BClO rapidly and significantly enhances after the addition of sodium hypochlorite, which shows the probe BClO is applicable for detecting hypochloric acid in living cells.

BClO Performance Measurement Experiment 8
Study on Probe BClO in Detecting Endogenous Hypochloric Acid in Raw264.7 Cells Raw264.7 cells were cultured in DEME (invitrogen) containing 10% FCS (invitrogen). On the day before the fluorescence confocal imaging experiment, the cells were inoculated in a specialized confocal cell culture dish. On the next day, 1 µM of the probe BClO was added therein, the cells were incubated for 20 minutes under the conditions of 37° C. and 5% $CO_2$ and then rinsed with a phosphate buffer solution for three times, and the confocal imaging was carried out. Under the same conditions, Raw264.7 cells were incubated with 1 µg/mL of LPS (lipopolysaccharide) for 12 hours and then incubated with 1 µg/mL of PMA (phorbol myristate acetate) for 1 hour, 1 µM of the probe BClO was added therein, the cells were incubated for 20 minutes under the conditions of 37° C. and 5% $CO_2$ and then rinsed with a phosphate buffer solution for three times, and the confocal imaging was carried out.

The culture density of cells was $2\times10^5$ cells/mL. The imaging instrument was Olympus FV1000-IX81 inverted microscope with oil lens of 100 times magnification. The fluorescence was exited at 488 nm, and the fluorescence at a wavelength range from 490 to 550 nm was collected.

Figure 8:
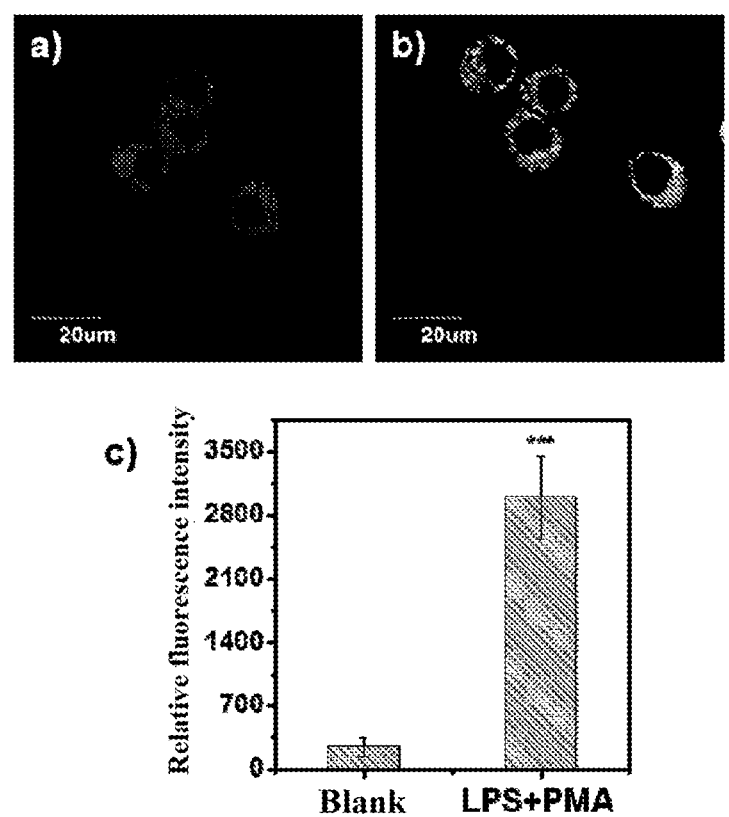
FIG. 8 shows fluorescence imaging pictures of the probe BClO in mice macrophage (Raw264.7) cells in the BClO performance measurement experiment 8. The level of the fluorescent probe BClO is 1 μM.

FIG. 8, panel a and panel b are fluorescence pictures of BClO in Raw264.7 cells before and after the stimulation of LPS and PMA. In order to quantify the fluorescent intensity change of BClO in cells, four regions were chosen from each figure to calculate the average value of the relative fluorescent intensity, and the results are shown in FIG. 8, panel c. It can be seen from the figure that, the probe BClO emits very weak green fluorescence in the macrophage cells due to a very small amount of reactive oxygen species in Raw264.7 cells, while the fluorescent intensity of the probe BClO significantly enhances after the stimulation of LPS and PMA, which shows the probe BClO is applicable for detecting endogenous hypochloric acid in living cells.

The invention claimed is:

1. A difluoroboron dipyrromethene fluorescent probe of formula I:

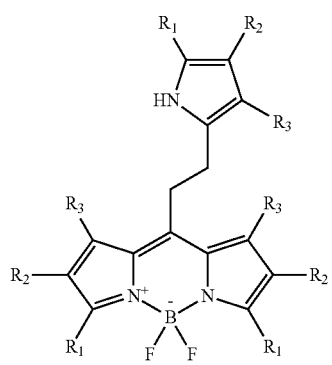

wherein in the formula I, $R_1$, $R_2$ and $R_3$ are each independently selected from the group consisting of H, $C_{1-8}$ alkyl, and substituted or unsubstituted phenyl, and said substituted phenyl is substituted at an optional location with one or more substituents selected from the group consisting of CN, COOH, $NH_2$, $NO_2$, OH, SH, $C_{1-6}$ alkoxy, $C_{1-6}$ alkylamino, $C_{1-6}$ amido, halogen, and $C_{1-6}$ haloalkyl.

2. The difluoroboron dipyrromethene fluorescent probe according to claim 1, wherein said $R_1$ and $R_3$ are each independently selected from the group consisting of H and methyl.

3. The difluoroboron dipyrromethene fluorescent probe according to claim 2, wherein said $R_1$ and $R_3$ are both methyl.

4. The difluoroboron dipyrromethene fluorescent probe according to claim 1, wherein said $R_2$ is selected from the group consisting of H and ethyl.

5. The difluoroboron dipyrromethene fluorescent probe according to claim 2, wherein said $R_2$ is selected from the group consisting of H and ethyl.

6. The difluoroboron dipyrromethene fluorescent probe according to claim 3, wherein said $R_2$ is selected from the group consisting of H and ethyl.

7. The difluoroboron dipyrromethene fluorescent probe according to claim 4, wherein said $R_2$ is H.

8. The difluoroboron dipyrromethene fluorescent probe according to claim 5, wherein said $R_2$ is H.

9. The difluoroboron dipyrromethene fluorescent probe according to claim 6, wherein said $R_2$ is H.

10. A method for producing the difluoroboron dipyrromethene fluorescent probe according to claim 1, comprising the steps of:

reacting a compound of formula II with acryloyl chloride in a molar ratio ranging from 1:1 to 5:1, and

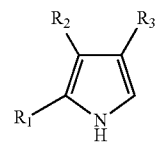

complexing the resultant reaction product with boron trifluoride in the presence of a base to obtain said difluoroboron dipyrromethene fluorescent probe.

11. The production method according to claim 10, wherein the compound having the formula II is reacted with acryloyl chloride in a molar ratio of 3:1.

12. A method of detecting a hypochlorite ion comprising use of the difluoroboron dipyrromethene fluorescent probe according to claim 1.

13. The method according to claim 12, wherein said difluoroboron dipyrromethene fluorescent probe is applied to detect a hypochlorite ion in living cells.

* * * * *